US007981145B2

(12) United States Patent
Korb et al.

(10) Patent No.: US 7,981,145 B2
(45) Date of Patent: Jul. 19, 2011

(54) TREATMENT OF MEIBOMIAN GLANDS (75) Inventors: Donald R. Korb, Boston, MA (US); Timothy R. Willis, Raleigh, NC (US); Stephen M. Grenon, Hillsborough, NC (US)

(73) Assignee: TearScience Inc., Morrisville, NC (US)

( * ) Notice: Subject to any disclaimer, the term of this patent is extended or adjusted under 35 U.S.C. 154(b) by 1116 days.

(21) Appl. No.: 11/541,418

(22) Filed: Sep. 29, 2006

(65) Prior Publication Data
US 2007/0027431 A1  Feb. 1, 2007

Related U.S. Application Data

(63) Continuation-in-part of application No. 11/434,054, filed on May 15, 2006, and a continuation-in-part of application No. 11/434,033, filed on May 15, 2006, and a continuation-in-part of application No. 11/434,446, filed on May 15, 2006, now abandoned.

(60) Provisional application No. 60/700,233, filed on Jul. 18, 2005.

(51) Int. Cl.
*A61M 35/00* (2006.01)
*A61F 7/02* (2006.01)
*A61F 7/08* (2006.01)

(52) U.S. Cl. ........... 607/96; 604/294; 604/298; 128/898

(58) Field of Classification Search .................... 604/289
See application file for complete search history.

(56) References Cited

U.S. PATENT DOCUMENTS

| 1,006,945 A | 10/1911 | Houston |
| 1,924,315 A | 8/1933 | Hemphill et al. |
| 2,891,252 A | 6/1959 | Lazo |
| 3,333,586 A | 8/1967 | Bellis et al. |
| 3,404,678 A | 10/1968 | Von Ardenne |

(Continued)

FOREIGN PATENT DOCUMENTS

CA  2679448 A1  9/2008

(Continued)

OTHER PUBLICATIONS

Paugh, J.R. et al., "Meibomian Therapy in Problematic Contact Lens Wear," Entrez PubMed, Optom Vis Sci. Nov. 1990; 68(11):803-6, 1 page.

(Continued)

*Primary Examiner* — Roy Gibson
*Assistant Examiner* — Kaitlyn Smith
(74) *Attorney, Agent, or Firm* — Withrow & Terranova, PLLC (57) ABSTRACT

In one embodiment consistent with the present invention a method of treating mammalian meibomian glands involves clearing the glands by applying a regulated heat to an eyelid containing the meibomian glands to a temperature adequate to melt obstructions in the meibomian glands to put the obstructions in a fluid or suspension (melted) state and maintaining the heat for a time period adequate to melt the obstructions. The glands can then be mechanically treated to express fluid from the glands, wherein the treating is carried out either during the time period or after the time period but while the obstruction remains in a fluid state. Subsequent pharmacological treatment of the glands by use of a pharmacological agent (topical or systemic) can then be used to assist in maintaining proper flow of lipids from the glands. This abstract is not to be considered limiting, since other embodiments may deviate from the features described in this abstract.

50 Claims, 3 Drawing Sheets

U.S. PATENT DOCUMENTS

| | | | |
|---|---|---|---|
| 3,667,476 A | 6/1972 | Muller | |
| 4,261,364 A | 4/1981 | Hadaddad et al. | |
| 4,778,457 A | 10/1988 | York | |
| 4,883,454 A | 11/1989 | Hamburg | |
| 4,914,088 A | 4/1990 | Glonek et al. | |
| 4,955,377 A | 9/1990 | Lennox et al. | |
| 4,958,632 A | 9/1990 | Duggan | |
| 5,030,214 A | 7/1991 | Spector | |
| 5,151,100 A | 9/1992 | Abele et al. | |
| 5,158,082 A | 10/1992 | Jones | |
| 5,213,097 A | 5/1993 | Zeindler | |
| 5,251,627 A | 10/1993 | Morris | |
| 5,283,063 A | 2/1994 | Freeman | |
| 5,343,561 A | 9/1994 | Adamo | |
| D352,106 S | 11/1994 | Fanney et al. | |
| 5,368,582 A | 11/1994 | Bertera | |
| 5,368,591 A | 11/1994 | Lennox et al. | |
| 5,425,380 A | 6/1995 | Hudson et al. | |
| 5,496,311 A | 3/1996 | Abele et al. | |
| 5,601,548 A | 2/1997 | Smith et al. | |
| 5,643,336 A | 7/1997 | Lopez-Claros | |
| 5,700,238 A | 12/1997 | Hyson | |
| 5,720,773 A | 2/1998 | Lopez-Claros | |
| 5,807,357 A | 9/1998 | Kang | |
| 5,836,927 A | 11/1998 | Fried | |
| 5,958,912 A | 9/1999 | Sullivan | |
| 5,964,723 A | 10/1999 | Augustine | |
| 6,024,095 A | 2/2000 | Stanley, III | |
| 6,107,289 A | 8/2000 | Sullivan | |
| 6,110,292 A | 8/2000 | Jewett et al. | |
| 6,112,900 A | 9/2000 | Adkins, Jr. | |
| 6,113,561 A | 9/2000 | Augustine | |
| 6,153,607 A | 11/2000 | Pflugfelder et al. | |
| 6,155,995 A | 12/2000 | Lin | |
| 6,181,970 B1 | 1/2001 | Kasevich | |
| 6,193,740 B1 | 2/2001 | Rodriguez | |
| 6,206,842 B1 | 3/2001 | Tu et al. | |
| 6,213,966 B1 | 4/2001 | Augustine | |
| 6,273,886 B1 | 8/2001 | Edwards et al. | |
| D456,079 S | 4/2002 | Fujii | |
| 6,423,018 B1 | 7/2002 | Augustine | |
| 6,425,888 B1 | 7/2002 | Embleton et al. | |
| 6,438,398 B1 | 8/2002 | Pflugfelder et al. | |
| 6,455,583 B1 | 9/2002 | Pflugfelder et al. | |
| 6,482,203 B2 * | 11/2002 | Paddock et al. | 606/41 |
| 6,490,488 B1 | 12/2002 | Rudie et al. | |
| D472,637 S | 4/2003 | Cooper et al. | |
| 6,544,257 B2 | 4/2003 | Nagase et al. | |
| D477,084 S | 7/2003 | Menezes et al. | |
| 6,641,264 B1 | 11/2003 | Schwebel | |
| 6,788,977 B2 | 9/2004 | Fenn et al. | |
| 6,827,898 B1 | 12/2004 | Fausset et al. | |
| 6,840,954 B2 | 1/2005 | Dietz et al. | |
| 6,860,852 B2 | 3/2005 | Schonenberger et al. | |
| 6,860,880 B2 | 3/2005 | Treat et al. | |
| 6,874,884 B2 | 4/2005 | Schwebel | |
| 6,882,885 B2 | 4/2005 | Levy, Jr. et al. | |
| 6,886,933 B2 | 5/2005 | Schwebel | |
| 6,908,195 B2 | 6/2005 | Fuller | |
| 6,925,317 B1 | 8/2005 | Samuels et al. | |
| 6,974,454 B2 | 12/2005 | Hooven | |
| 7,001,379 B2 | 2/2006 | Behl et al. | |
| 7,004,942 B2 | 2/2006 | Laird et al. | |
| 7,036,928 B2 | 5/2006 | Schwebel | |
| 7,069,084 B2 | 6/2006 | Yee | |
| 7,108,694 B2 | 9/2006 | Miura et al. | |
| 7,118,591 B2 | 10/2006 | Frank et al. | |
| 7,123,968 B1 | 10/2006 | Casscells, III et al. | |
| 7,211,070 B2 | 5/2007 | Soroudi | |
| 7,231,922 B2 | 6/2007 | Davison et al. | |
| D546,459 S | 7/2007 | Banryu | |
| D552,736 S | 10/2007 | Yamaoka | |
| D553,750 S | 10/2007 | Yamaoka | |
| 7,357,500 B2 | 4/2008 | Schwebel | |
| 7,442,174 B2 | 10/2008 | Butler | |
| 7,513,893 B2 | 4/2009 | Soroudi | |
| 7,594,728 B2 | 9/2009 | Seal et al. | |
| D612,941 S | 3/2010 | Youngquist et al. | |
| D614,774 S | 4/2010 | Gausmann et al. | |
| 7,712,899 B2 | 5/2010 | Tanassi et al. | |
| 2001/0041886 A1 | 11/2001 | Durkin et al. | |
| 2002/0035345 A1 | 3/2002 | Beck | |
| 2002/0099094 A1 * | 7/2002 | Anderson | 514/561 |
| 2002/0111608 A1 | 8/2002 | Baerveldt et al. | |
| 2002/0128696 A1 | 9/2002 | Pearl et al. | |
| 2003/0056281 A1 * | 3/2003 | Hasegawa | 2/428 |
| 2003/0065277 A1 * | 4/2003 | Covington | 600/573 |
| 2003/0114426 A1 | 6/2003 | Pflugfelder et al. | |
| 2003/0139790 A1 | 7/2003 | Ingle et al. | |
| 2003/0195438 A1 | 10/2003 | Petillo | |
| 2003/0211043 A1 | 11/2003 | Korb | |
| 2003/0233135 A1 | 12/2003 | Yee | |
| 2004/0064169 A1 | 4/2004 | Briscoe et al. | |
| 2004/0064171 A1 | 4/2004 | Briscoe et al. | |
| 2004/0076695 A1 | 4/2004 | Gilbard | |
| 2004/0111138 A1 | 6/2004 | Bleam et al. | |
| 2004/0153093 A1 | 8/2004 | Donovan | |
| 2004/0237969 A1 * | 12/2004 | Fuller | 128/858 |
| 2004/0249427 A1 | 12/2004 | Nabilsi | |
| 2005/0022823 A1 | 2/2005 | Davison et al. | |
| 2005/0119629 A1 * | 6/2005 | Soroudi | 604/289 |
| 2005/0143798 A1 | 6/2005 | Bleam et al. | |
| 2005/0220742 A1 | 10/2005 | Breen | |
| 2006/0018953 A1 * | 1/2006 | Guillon et al. | 424/443 |
| 2006/0030604 A1 | 2/2006 | Elsinger et al. | |
| 2006/0055878 A1 | 3/2006 | Yee | |
| 2006/0104914 A1 | 5/2006 | Soroudi | |
| 2006/0139569 A1 | 6/2006 | Schwebel | |
| 2006/0154901 A1 | 7/2006 | Pflugfelder et al. | |
| 2006/0157064 A1 | 7/2006 | Davison et al. | |
| 2006/0183698 A1 | 8/2006 | Abelson | |
| 2006/0233859 A1 * | 10/2006 | Whitcup et al. | 424/427 |
| 2007/0016256 A1 | 1/2007 | Korb et al. | |
| 2007/0049913 A1 | 3/2007 | Grenon et al. | |
| 2007/0173799 A1 | 7/2007 | Hsia | |
| 2007/0203462 A1 | 8/2007 | Soroudi | |
| 2007/0280924 A1 | 12/2007 | Daniels et al. | |
| 2008/0051741 A1 | 2/2008 | Grenon et al. | |
| 2008/0075787 A1 | 3/2008 | Hibino | |
| 2008/0132973 A1 | 6/2008 | Lord et al. | |
| 2009/0043365 A1 | 2/2009 | Friedland et al. | |
| 2009/0137533 A1 | 5/2009 | Adkins, Jr. | |
| 2009/0306111 A1 | 12/2009 | Nakamura et al. | |
| 2010/0100029 A1 | 4/2010 | Maskin | |
| 2010/0292630 A1 | 11/2010 | Maskin | |
| 2011/0039805 A1 | 2/2011 | Pflugfelder et al. | |
| 2011/0059902 A1 | 3/2011 | Sullivan et al. | |
| 2011/0059925 A1 | 3/2011 | Donnenfeld | |

FOREIGN PATENT DOCUMENTS

| | | |
|---|---|---|
| DE | 202005011496 U1 | 7/2006 |
| EP | 2151438 A1 | 2/2010 |
| EP | 1587468 B1 | 1/2011 |
| JP | 06269473 | 9/1994 |
| JP | 411221247 | 8/1999 |
| JP | 02002078727 | 3/2002 |
| JP | 2006 198249 | 8/2006 |
| JP | 2010155012 A | 7/2010 |
| WO | 99/58131 A1 | 11/1999 |
| WO | PCT/US99/09965 | 11/1999 |
| WO | 2004/041134 A1 | 5/2004 |
| WO | PCT/GB/2003/004782 | 5/2004 |
| WO | 2008024100 A2 | 2/2008 |
| WO | 2008106228 A2 | 9/2008 |
| WO | 2009064834 A2 | 5/2009 |

OTHER PUBLICATIONS

Korb, Donald et al., "The Effect of Two Novel Lubricant Eye Drops on Tear Film Lipid Layer Thickness in Subjects with Dry Eye Symptoms," Optom. Vis. Sci., vol. 82, No. 7, 2005, pp. 594-601.

Korb, Donald R. et al., "Tear Film Lipid Layer Thickness as a Function of Blinking," Cornea, vol. 13, No. 4, 1994, pp. 354-359.

Knop, E. et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).

Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).

Blackie, Caroline A. et al., "Recovery Time of an Optimally Secreting Meibomian Gland," Cornea, vol. 28, No. 3, Apr. 2009, pp. 293-297.

"New Over-the-Counter Dry Eye Drop Now Available to Help Estimated 40 Percent of Americans Who Suffer from Occasional or Chronic Dry Eye" Business Wire News Release, Published Mar. 31, 2008.

Gupta, S. et al. "Docetaxel-induced Meibomian Duct Inflammation and Blockage Leading to Chalazion Formation" Prostate Cancer Prostatic Diseases, vol. 10, No. 4, 2007.

Aronowicz, J D et al. "Short Term Oral Minocycline Treatment of Meibomiantis" Br. J Opthalmol, vol. 90, No. 7, Jul. 2006.

Goto, E. et al, "Treatment of Non-Inflamed Obstructive Meibomian Gland Dysfunction by an Infrared Warm Compression Device" Br J Opthalmol, vol. 86, No. 12, Dec. 2002.

"arGentis Licenses Third Treatment for Dry Eye Syndrome" www.businesswire.com, May 12, 2008.

Meibomian Gland Dysfunction and Contact Lens Intolerance, Korb et al., Journal of the American Optometric Association, vol. 51, No. 3 Mar. 1980 p. 243-251.

Impact of Antiandrogen Treatment on the Fatty Acid Profile of Neutral Lipids in Human Meibomian Gland Secretions, Sullivan et al, Jnl. Clinical Endocrinogy & Metabolism, vol. 85, No. 12 p. 4866-4873, 2000.

Tear Film Lipid Layer Thickness and Ocular Comfort After Meibomian Therapy via Latent Heat with a Novel Device in Normal Subjects, Mitra et al., Eye (2004) 1-4.

Increase in Tear Film Lipid Layer Thickness Following Treatment of Meibomian Gland Dysfunction, Korb & Greiner, Lacrimal Gland, Tear Film & Dry Eye Syndromes, Plenum Press, 1994 pp. 293-298.

Poster 349-B349 Efficacy of the Treatment by the Disposable Eyelid Warming Instrument for Meibomian Gland Dysfunction, Goto et al., Sunday Apr. 30.

Disposable Eyelid-Warming Device for Treatment of Meibomina Gland Dysfunction, Mori, et al., Japan Journal of Ophthalmology, vol. 47, p. 578-586 (2003).

Conservative Treatment of Meibomian Gland Dysfunction, Romero et al. Contact Lens Ass'n of Ophthalmology, p. 14-19, Eye & Contact Lens vol. 30, p. 14-19 (2004).

The Therapeutic Role of Lipids-Managing Ocular Surface Disease, Lemp & Foulks, Supplement to Refractive Eyecare of Ophthalmologists, vol. 9, No. 6, Jun. 2005.

Treatment of non-inflamed Obstructive Meiboman Gland Dysfunction by an Infrared Warm Compression Device; Goto, et al., Br. J. Opthalmology 2002:86: 1403-1407.

Tear Evaoporation Dynamics in Normal Subjects and Subjects with Obstructive Meibomian Gland Dysfunction; Goto et al., Investigative Opthalmology & Visual Science, Feb. 2003, vol. 44, No. 2, p. 533-539.

Conservative Treatment of Meibomian Gland Dysfunction; Romero et al. Eye & Contact Lens30(1):14-19, 2004.

Tear Function Changes of Postmenopausal Women in Response to Hormone Replacement Therapy, Kuscu et al, Maturitas 44 (2003) 63-68.

Increase in Tear Film Lipid Layer Thickness Following Treatment with Warm Compresses in Patients with Meibomian Gland Dysfunction, Olson et al., Eye & Contact Lens 29(2): 96-99, 2003.

Blackie, Caroline A. et al., "Inner Eyelid Surface Temperature as a Function of Warm Compress Methodology," Optometry and Vision Science, vol. 85, No. 8, Aug. 2008, pp. 675-683.

Kokke, K.H. et al., "Oral Omega-6 Essential Fatty Acid Treatment in Contact Lens Associated Dry Eye," Contact Lens and Anterior Eye, vol. 31, No. 3, 2008, pp. 141-146.

Korb, Donald R., Slide entitled "Inner Eyelid Surface Temperature as a Function of Warm Compress Methodology," from presentation entitled "The Tear Film and Dry Eye States a Fertile Research Area," University of California at Berkeley, School of Optometry, Apr. 11, 2008. 2 pages.

Korb, Donald R. et al., Slide entitled "Inner Eyelid Surface Temperature as a Function of Warm Compress Methodology," from presentation entitled "The Greatest Anterior Segment Disease and Contact Lens Complications Course," AOA Meeting, Seattle, Washington, Jun. 27, 2008, 2 pages.

Sullivan, David et al., "Do Sex Steroids Exert Sex-Specific and/or Opposite Effects on Gene Expression in Lacrimal and Meibomian Glands?" Molecular Vision, vol. 15, No. 166, Aug. 10, 2009, pp. 1553-1572.

Paugh, Jerry R. et al., "Precorneal Residence Time of Artificial Tears Measured in Dry Eye Subjects," Optometry and Vision Science, vol. 85, No. 8, Aug. 2008, pp. 725-731.

Lemp, Michael A. et al., "Blepharitis in the United States 2009: A Survey-Based Perspective on Prevalence and Treatment." Ocul. Surf, vol. 7, No. 2 Suppl, Apr. 2009, pp. S1-S14.

Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.

Toyos, Rolando, "Intense Pulsed Light for Dry Eye Syndrome," Cataract & Refractive Surgery Today, Apr. 2009, pp. 1-3.

Donnenfeld, Eric et al., "Topical Ophthalmic Cyclosporine: Pharmacology and Clinical Uses," Survey of Ophthalmology, vol. 54, No. 3, May/Jun. 2009, pp. 321-338.

Suzuki, Tomo et al., "Estrogen and Progesterone Control of Gene Expression in the Mouse Meibomian Gland," Invest. Ophthalmol. Vis. Sci., vol. 49, No. 5, Apr. 2008, pp. 1797-1818.

Vasta, Stephanie, "Aggressive Treatments Developed for Meibomian Gland Dysfunction," Primary Care Optometry News, Nov. 1, 2009, 3 pages.

Foulks, Gary N. et al., "Topical Azithromycin Therapy for Meibomian Gland Dysfunction: Clinical Response and Lipid Alterations," Cornea, vol. 29, No. 7, Jul. 2010, pp. 781-788.

Butovich, Igor et al., "Meibomian Lipid Glands and the Impact of Temperature," Investigative Opthalmology & Visual Science, vol. 51, No. 11, Nov. 2010, pp. 5508-5518.

Korb, Donald R. et al., "Restoration of Meibomian Gland Functionality with Novel Thermodynamic Treatment Device—A Case Report," Cornea, vol. 29, No. 8, Aug. 2010, pp. 930-933.

Akyol-Salman, Ilknur et al., "Efficacy of Topical N-Acetylcysteine in the Treatment of Meibomian Gland Dysfunction," Journal of Ocular Pharmacology and Therapeutics, vol. 26, No. 4, Aug. 1, 2010, pp. 329-333.

Wang, Y. et al., "Baseline Profiles of Ocular Surface and Tear Dynamics After Allogeneic Hematopoietic Stem Cell Transplantation in Patients With or Without Chronic GVHD-Related Dry Eye," Bone Marrow Transplantation, vol. 45, No. 6, Jun. 2010, pp. 1077-1083.

Korb, Donald R. et al., "Lid Wiper Epitheliopathy and Dry Eye Symptoms," Eye & Contact Lens, vol. 31, No. 1, 2005, pp. 2-8.

Foulks, Gary N., "Meibomian Gland Dysfunction: The Past, Present, and Future," Eye and Contact Lens, vol. 36, No. 5, Sep. 2010, pp. 249-253.

Blackie, Caroline A. et al., "Nonobvious Obstructive Meibomian Gland Dysfunction" Cornea, vol. 29, No. 12, Dec. 2010, pp. 1333-1345.

Haque, Reza M. et al., "Multicenter Open-label Study Evaluating the Efficacy of Azithromycin Opthalmic Solution 1% on the Signs and Symptoms of Subjects with Blepharitis," Cornea, vol. 29, No. 8, Aug. 2010, pp. 871-877.

Maskin, Steven L., "Intraductal Meibomian Gland Probing Relieves Symptoms of Obstructive Meibomian Gland Dysfunction," Cornea, vol. 29, No. 10, Oct. 2010, pp. 1145-1152.

Dausch, Eva et al., "Dry Eye Syndrome in Women's Health and Gynecology: Etiology, Pathogenesis and Current Therapeutic Strategies," Geburtshilfe und Frauenheilkunde, vol. 70, No. 9, Jan. 1, 2010, pp. 707-711. (Abstract Only).

Friedland, B., et al., "A novel thermodynamic treatment for meibomian gland dysfunction," Current Eye Research, vol. 36, No. 2, Feb. 2011, pp. 79-87.

Non-Final Rejection mailed Jun. 17, 2009, for U.S. Appl. No. 11/434,446.

Final Rejection mailed Dec. 23, 2009, for U.S. Appl. No. 11/434,446.

Advisory Action mailed Mar. 4, 2010, for U.S. Appl. No. 11/434,446.

Non-Final Rejection mailed Apr. 9, 2010, for U.S. Appl. No. 11/434,446.
Restriction/Election Requirement mailed Oct. 1, 2010, for U.S. Appl. No. 11/434,033.

Non-Final Rejection mailed Jan. 24, 2011, for U.S. Appl. No. 11/434,033.

* cited by examiner

TREATMENT OF MEIBOMIAN GLANDS

CROSS REFERENCE TO RELATED DOCUMENTS

This application is a Continuation-In-Part of U.S. patent application Ser. No. 11/434,054, filed May 15, 2006 and entitled Method and Apparatus for Treating Meibomian Gland Dysfunction to Korb, et al., which claims priority benefit of U.S. Provisional Application No. 60/700,233, filed Jul. 18, 2005, and is further a Continuation-in-part of U.S. patent application Ser. No. 11/434,033, filed May 15, 2006 entitled Method and Apparatus for Treating Gland Dysfunction Employing Heated Medium, to Grenon, et al. and is further a Continuation-in-part of U.S. patent application Ser. No. 11/434,446, filed May 15, 2006 now abandoned entitled Method and Apparatus for Treating Gland Dysfunction to Korb, et al., each of which is hereby incorporated by reference in its entirety.

COPYRIGHT NOTICE

A portion of the disclosure of this patent document contains material which is subject to copyright protection. The copyright owner has no objection to the facsimile reproduction of the patent document or the patent disclosure, as it appears in the Patent and Trademark Office patent file or records, but otherwise reserves all copyright rights whatsoever.

FIELD

This invention relates generally to treatment of mammalian eyes. More particularly, this invention relates treatments of obstruction of meibomian glands by use of various combinations of heat to melt certain obstructions (or melt material binding solid particles forming an obstruction), mechanical action to clear the obstruction and pharmaceutical treatment once the obstruction has been cleared.

BACKGROUND

The human body contains a number of glands including the lacrimal and meibomian glands of the eye, the sebaceous or pilo-sebaceous hair glands on the face and underarms, and the mammary glands in the breasts. These glands may malfunction due to age, irritation, environmental conditions, cellular debris, inflammation, hormonal imbalance and other causes. One common disease state of the eyelid glands is the restriction or stoppage of the natural flow of fluid out of the gland caused by an obstruction.

In the human eye, the tear film covering the ocular surfaces is composed of three layers. The innermost layer in contact with the ocular surface is the mucus layer comprised of many mucins. The middle layer comprising the bulk of the tear film is the aqueous layer, and the outermost layer is a thin (less than 250 nm) layer comprised of many lipids known as "meibum" or "sebum". The sebum is secreted by the meibomian glands, enlarged specialized sebaceous-type glands (hence, the use of "sebum" to describe the secretion) located within both the upper and lower eye lids, with orifices designed to discharge the lipid secretions onto the lid margins, thus forming the lipid layer of the tear film. The typical upper eyelid has about 25 meibomian glands and the lower eyelid has about 20 meibomian glands, which are somewhat larger than those located in the upper lid. The meibomian gland comprises various sac-like acini which discharge the secretion into the main central duct of the gland. The secretion then passes into the orifices which are surrounded by smooth muscle tissue and the muscle of Riolan which are presumed to aid in the expression of sebum. The meibomian gland orifices open onto the lid margin at and around the junction of the inner mucous membrane and the outer skin of the eyelids termed the mucocutaneous junction.

Specifically, as illustrated in the above patent applications, each meibomian gland has a straight long central duct lined with four epithelial layers on the inner surface of the duct. Along the length of the central duct there are multiple lateral out-pouching structures, termed acini where the secretion of the gland is manufactured. The inner lining of each acinus differs from the main central duct in that these specialized cells provide the secretions of the meibomian gland. The secretions flow from each acinus to the duct. While it has not been established with certainty, there appears to be a valve system between each acinus and the central duct to retain the secretion until it is required, at which time it is discharged in to the central duct. The meibomian secretion is then stored in the central duct and is released through the orifice of each gland onto the lid margin. Blinking and the squeezing action of the muscle of Riolan surrounding the meibomian glands are thought to be the primary mechanism to open the orifice for the release of secretion from the meibomian gland.

The upward phase of blinking causes the upper lid to pull a sheet of the lipids secreted by the meibomian glands upward and over the other two layers of the tear film, thus forming a type of protective coating which limits the rate at which the underlying layers evaporate. Thus, it will be seen that a defective lipid layer or an incorrect quantity of such lipids can result in accelerated evaporation of the aqueous layer which, in turn, causes symptoms such as itchiness, burning, irritation, and dryness, which are collectively referred to as "dry eye".

Dry eye states have many etiologies. A common cause of common dry eye states is a disorder where the glands are obstructed or occluded, usually referred to as "meibomian gland dysfunction" (MGD). As employed herein the terms "occluded" and "obstruction" as they relate to meibomian gland dysfunction are defined as partially or completely blocked or plugged meibomian glands, or any component thereof, having a solid, semi-solid or thickened congealed secretion and/or plug, leading to a compromise, or more specifically, a decrease or cessation of secretion. Also with a reduced or limited secretion the meibomian gland may be compromised by the occluded or obstructive condition as evidenced by a yellowish color indicating a possible infection state, or may be otherwise compromised so that the resulting protective lipid protective film is not adequate.

Meibomitis, an inflammation of the meibomian glands leading to their dysfunction, is usually accompanied by blepharitis (inflammation of the lids). Meibomian gland dysfunction may accompany meibomitis, or meibomian gland dysfunction may be present without obvious lid inflammation. Meibomian gland dysfunction is frequently the result of keratotic obstructions which partially or completely block the meibomian gland orifices and/or the central duct (canal) of the gland, or possibly the acini or acini valves (assuming they do in fact exist) or the acini's junction with the central duct. Such obstructions compromise the secretory functions of the individual meibomian glands. More particularly, these keratotic obstructions can comprise combination of bacteria, sebaceous ground substance, dead, and/or desquamated epithelial cells, see, Korb et al., Meibomian Gland Dysfunction and Contact Lens Intolerance, Journal of the Optometric Association, Vol. 51, Number 3, (1980), pp. 243-251. While meibomitis is obvious by inspection of the external lids, meibomian gland dysfunction may not be obvious even when examined with the magnification of the slit-lamp biomicroscope, since there may not be external signs, or the external signs may be so minimal that they are overlooked. The external signs of meibomian gland dysfunction without obvious lid inflammation may be limited to subtle alterations of the meibomian gland orifices, overgrowth of epithelium over the orifices, and pouting of the orifices of the glands with congealed material acting as obstructions. In severe instances of meibomian gland dysfunction without obvious lid inflammation the changes may be obvious, including serrated or undulated lid margins, orifice recession and more obvious overgrowth of epithelium over the orifices, and pouting of the orifices.

Hormonal changes, which occur during menopause, and particularly changing estrogen levels, can result in thickening of the oils secreted by the meibomian glands which results in clogged gland orifices. Further, decreased estrogen levels may also enhance conditions under which staphylococcal bacteria can proliferate. This can cause migration of the bacteria into the glands, thus resulting in a decreased secretion rate.

When the flow of secretions from the meibomian gland is restricted due to the existence of an obstruction, cells on the eyelid margin have been observed to grow over the gland orifice thus further restricting sebum flow and exacerbating the dry eye condition. Additional factors which may cause or exacerbate meibomian gland dysfunction include, age, disorders of blinking, activities such as computer use which compromise normal blinking, contact lens wear and hygiene, cosmetic use, or other illness, particularly diabetes.

The state of an individual meibomian gland can vary from optimal, where clear meibomian fluid is produced; to mild or moderate meibomian gland dysfunction where milky fluid or inspissated or creamy secretion is produced; to total blockage where no secretion of any sort can be obtained (see Korb, et al., "Increase in Tear Film Lipid Layer Thickness Following Treatment of Meibomian Gland Dysfunction", Lacrimal Gland, tear Film, and Dry Eye Syndromes, pp. 293-298, Edited by D. A. Sullivan, Plenum Press, New York (1994)). Significant chemical changes of the meibomian gland secretions occur with meibomian gland dysfunction and consequently, the composition of the naturally occurring tear film is altered, which in turn, contributes to ocular disease which is generally known as "dry eye".

While the tear film operates as a singular entity and all of the layers thereof are important, the lipid layer, which is secreted from the meibomian glands, is of particular significance as it functions to slow the evaporation of the underlying layers and to lubricate the eyelid during blinking which prevents dry eye.

Thus, to summarize, the meibomian glands of mammalian (e.g., human) eyelids secrete oils that prevent evaporation of the tear film and provide lubrication to the eye and eyelids. These glands can become blocked or plugged by various mechanisms leading to so-called "dry eye syndrome". While not the only cause, meibomian gland dysfunction (MGD) is known to be a major cause of dry eye syndrome. The disorder is characterized by a blockage of some sort within the meibomian glands or at their surface preventing normal lipid secretions from flowing from the meibomian glands to form the lipid layer of the tear film.

Such secretions serve to prevent evaporation of the tear film and lubricate the eye and eyelids, hence their absence can cause dry eye syndrome. Obstructions or occlusions of the meibomian glands may be present over or at the orifice Of the gland, in the main channel of the gland which may be narrowed or blocked, or possibly in other locations including the passages from the acini to the main channel.

It has been theorized that the acini of the glands may have valves at their junction with the main channel of the gland. The inventors theorize that if these valves exist, they may also become obstructed in some instances leading to reduced or blocked flow from the acini. These obstructions or occlusions may have various compositions.

In response to the foregoing, various treatment modalities have been developed in order to treat the dry eye condition, including drops which are intended to replicate and replace the natural tear film, pharmaceuticals which are intended to stimulate the tear producing cells, and various heating devices which are designed to assist in unclogging the meibomian glands. Other techniques involve manual expression of the glands.

Eye drops such as Refresh®, Soothe® and Systane® brand eye drops are designed to closely replicate the naturally occurring healthy tear film. However, their use and administration is merely a treatment of symptoms and not of the underlying cause. Further, the use of drops is generally for an indefinite length of time and consequently, extended use can become burdensome and costly.

Pharmaceutical modalities such as the use of tetracycline have also been suggested to treat meibomian gland dysfunction and one such treatment is disclosed in United States Patent Publication no. US2003/011426 titled "Method for Treating Meibomian Gland Disease", U.S. Pat. No. 6,455,583 titled "Method for Treating Meibomian Gland Disease" to Pflugfelder et al. and PCT Publication No. WO 99/58131 titled "Use of Tetracyclines for Treating Meibomian Gland Disease". However, this treatment has not proven to be universally clinically effective, and it may be unnecessary in cases where meibomian gland dysfunction is the result of obstruction of the gland without infection. The use of corticosteroids have also been proposed to treat meibomian gland dysfunction as disclosed in U.S. Pat. No. 6,153,607 titled "Non-preserved Topical Corticosteroid for Treatment of Dry Eye, filamentary Keratitis, and Delayed Tear Clearance (or Turnover) to Pflugfelder et al. Again, this proposed treatment appears to treat the symptom of dry eye, as opposed to treatment of the underlying cause. Additionally, the use of topically applied androgens or androgen analogues have also been used to treat acute dry eye signs and symptoms in Keratoconjuctivitis Sicca as disclosed in U.S. Pat. No. 5,958,912 and U.S. Pat. No. 6,107,289 both titled "Ocular Therapy in Keratoconjunctivitis Sicca Using Topically Applied Androgens or TGF-β" and both issued to Sullivan.

Most knowledgeable doctors agree that heat is beneficial in treating MGD. Depending upon the nature of the obstruction, heat may be beneficial in actually melting or loosening the obstructing material, permitting the gland to begin production and excretion of lipids and other fluids more freely.

One modality for the heat treatment of meibomian gland dysfunction is disclosed in European Patent Application serial no. PCT/GB2003/004782 titled "Eyelid Margin Wipes Comprising Chemical Means for Temperature Adjustment". As disclosed in this patent application, a wipe is provided wherein prior to use, a chemical agent is activated that will heat the wipe to about 32° C. to about 40° C. The hot wipe is then applied to the lids and manual expression can then be used to unclog the ducts. This method is not without its drawbacks in that lid irritation can be exacerbated by non-specific heating.

Another method of heating the eyelids and meibomian glands uses near infrared (NIR) radiation. More specifically, two hard eye patches were attached to an eye mask according to the pupillary distance of the subject. The eye mask was held in place by an elastic headband. Each patch employed 19 light emitting diodes, emitting near infrared radiation from 850 nm to 1050 nm, with a peak at 940 nm. The device produced 10 mW/cm$^2$ of energy operating on electrical power. Goto, E., et al., Treatment of Non-Inflamed Obstructive Meibomian Gland dysfunction by an Infrared Warm Compression Device, British Journal of Ophthalmology, Vol. 86 (2002), pp. 1403-1407. This device is designed as a non-contact infrared heating mask using IR light emitting diodes. However, there are many potential problems with use of an IR heating mechanism. For example, the IR Heat can penetrate beyond the eyelid into the cornea which is undesirable, and could ultimately cause cataracts or other damage. Additionally, the IR mask heater places no pressure whatsoever on the eyelid (despite the description as a compression device) which we have determined is useful to expel the blockage. Moreover, tests conducted on a sample of this mask revealed that in spite of the potential dangers, the mask produced very little actual heat.

United States Patent Publication US2004/0237969 titled "Therapeutic Eye and Eye Lid Cover" comprises a pair of goggles that are adapted to deliver heated saturated air to the eyelids and particularly to the meibomian glands, again to heat the gland. Heat treatment of the eyes is also discussed in the article titled "Tear Film Lipid Layer Thickness and Ocular Comfort after Meibomian Therapy via Latent Heat with a Novel Device in Normal Subjects by Mitra et al, published in Eye, (2004) at pages 1-4.

United States Patent Publication US2003/0233135 titled "Method and Apparatus for Preventing and Treating Eyelid Problems" to Yee attempts to clear the plugged meibomian glands by means of electrical stimulation of the muscle of Riolan which the invention presumed to aid in the expression of the meibomian gland secretion.

SUMMARY OF CERTAIN EMBODIMENTS

It is an object of certain embodiments consistent with the present invention to provide a method for treatment of mammalian eyelids.

It is another object of certain embodiments consistent with the present invention to provide a method of treatment that first produces a flow of lipids from the meibomian glands of the upper and/or lower eyelids of either or both eyes in order to aid in the clearing of certain types of obstructions that may be present in or about the meibomian glands, followed by pharmacological treatment to assist in maintaining the flow of lipids or otherwise assist in the promoting lubrication of the eyes.

In one embodiment consistent with the present invention a method of treating mammalian meibomian glands involves clearing the glands by applying a regulated heat to an eyelid containing the meibomian glands to a temperature adequate to melt obstructions in the meibomian glands, thereby placing the obstruction in a fluid or suspension (melted) state, and maintaining the heat for a time period adequate to melt the obstructions and place the obstructions in the fluid or suspension (melted) state. The glands can then be mechanically treated to express fluid from the glands, wherein the treating is carried out either during the time period or after the time period but while the obstruction remains in the fluid or suspension state. In most instances, this should be carried out within about 90 seconds of the end of the time period. Subsequent pharmacological treatment of the glands by use a pharmacological agent (topical or systemic) can then be used to assist in maintaining proper flow of lipids from the glands or otherwise assist in the promoting lubrication of the eyes.

In accordance with certain embodiments, the time period can be approximately 10 to 60 minutes, and approximately 15 minutes is generally suitable for mild to moderate cases of MGD. In more severe cases, treatments of 30-45 minutes may be required, and for very severe cases, up to and beyond 60 minutes of heat treatment may be needed. These times assume a target temperature of 44-47 degrees with 45 degrees C. being preferred, and may possibly be reduced somewhat for higher temperatures or extended somewhat for lower temperatures. Temperatures can range from 37 degrees Celsius and up.

In certain embodiments, the mechanical treatment is carried out by at least one of application of constant pressure, vibratory energy, mechanical energy, pulsating mechanical stimulation, squeezing, milkingly expressing the fluid from one or more of the glands while simultaneously applying heat, or applying vibratory stimulation to the eyelid while simultaneously applying heat.

In another embodiment, a method of treating meibomian gland dysfunction in a mammal wherein an occlusion blocks at least a portion of the flow of naturally occurring secretions out of a gland channel orifice involves applying a regulated heat source proximate to the gland channel orifice for a selected time and at a selected temperature adequate to soften or liquefy at least a portion of the occlusion; mechanically treating the gland channel orifice while the at least a portion of the occlusion remains softened or liquefied such that at least a portion of the occlusion is removed; subsequently treating the mammal with a pharmacological agent which promotes the free flow of lipids from the meibomian gland or otherwise assist in the promoting lubrication of the eyes.

In another embodiment, a method of treating meibomian gland dysfunction in a mammal wherein an occlusion blocks at least a portion of the flow of naturally occurring secretions out of a gland channel orifice involves applying a regulated heat source proximate to the gland channel orifice for a selected time and at a selected temperature adequate to loosen, breakup, fracture, soften or liquefy at least a portion of the occlusion; mechanically treating the gland channel orifice prior to reversal of the effects of the application of the regulated heat source such that at least a portion of the occlusion is removed; subsequently treating the mammal with a pharmacological agent which promotes the free flow of lipids from the meibomian gland or otherwise assist in the promoting lubrication of the eyes.

The above overviews are intended to illustrate exemplary embodiments which will be best understood in conjunction with the detailed description to follow, and are not intended to limit the scope or meaning of the appended claims.

BRIEF DESCRIPTION OF THE DRAWINGS

Certain illustrative embodiments illustrating organization and method of operation, together with objects and advantages may be best understood by reference detailed description that follows taken in conjunction with the accompanying drawings in which.

DETAILED DESCRIPTION

While this invention is susceptible of embodiment in many different forms, there is shown in the drawings and will herein be described in detail specific embodiments, with the understanding that the present disclosure of such embodiments is to be considered as an example of the principles and not intended to limit the invention to the specific embodiments shown and described. In the description below, like reference numerals are used to describe the same, similar or corresponding parts in the several views of the drawings.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically. The term "program" or "computer program" or similar terms, as used herein, is defined as a sequence of instructions designed for execution on a computer system. A "program", or "computer program", may include a subroutine, a function, a procedure, an object method, an object implementation, in an executable application, an applet, a servlet, a source code, an object code, a shared library/dynamic load library and/or other sequence of instructions designed for execution on a computer system.

Reference throughout this document to "one embodiment", "certain embodiments", "an embodiment" or similar terms means that a particular feature, structure, or characteristic described in connection with the embodiment is included in at least one embodiment of the present invention. Thus, the appearances of such phrases or in various places throughout this specification are not necessarily all referring to the same embodiment. Furthermore, the particular features, structures, or characteristics may be combined in any suitable manner in one or more embodiments without limitation.

The term "or" as used herein is to be interpreted as an inclusive or meaning any one or any combination. Therefore, "A, B or C" means "any of the following: A; B; C; A and B; A and C; B and C; A, B and C". An exception to this definition will occur only when a combination of elements, functions, steps or acts are in some way inherently mutually exclusive.

As noted above, meibomian gland dysfunction (MGD) is known to be a major cause of dry eye syndrome. The disorder is characterized by a blockage of some sort within the meibomian glands preventing normal lipid secretions from flowing through the orifices and out of the glands to the tear film. Obstructions or occlusions of the meibomian glands may be present at the orifice of the gland, the main channel of the gland, or possibly in other locations including the main channel of the gland which may be narrowed or blocked. It has been theorized that the acini of the glands may have valves at their junction with the main channel of the gland, and that these valves may be obstructed in some instances-leading to reduced or blocked flow from the acini. These obstructions or occlusions may have various compositions.

Figure 1:
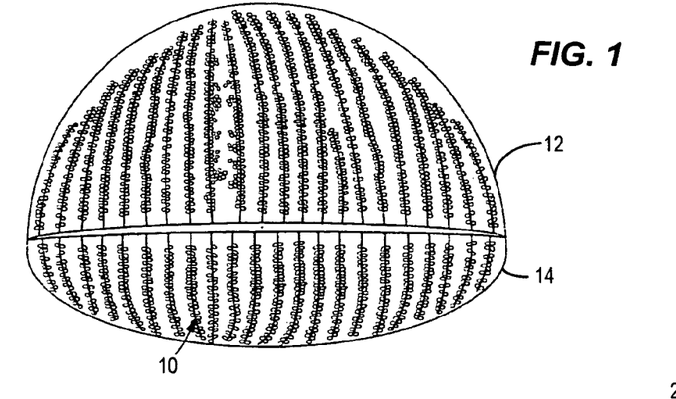
FIG. 1 depicts upper and lower human eyelids showing the meibomian glands.

Referring now to FIG. 1, the location of the meibomian glands 10 are shown on the upper and lower eyelids 12 and 14 respectively. As briefly stated herein above, the upper lid contains about 25 meibomian glands and the lower lid contains about 20 meibomian glands, with significant variation. As shown in cross-sectional view of one gland 10 in FIG. 2, each gland includes a central duct or channel 18 into which the secretion flows from acini 19 and an orifice 20 which opens on to the eyelid margin and through which the secretion flows in order to be added to the tear film upon blinking. It will be seen that the glands are of different size, depending upon the location in the eyelid and that the orifice 20 is narrower than the central duct 18.

Figures 2, 3:
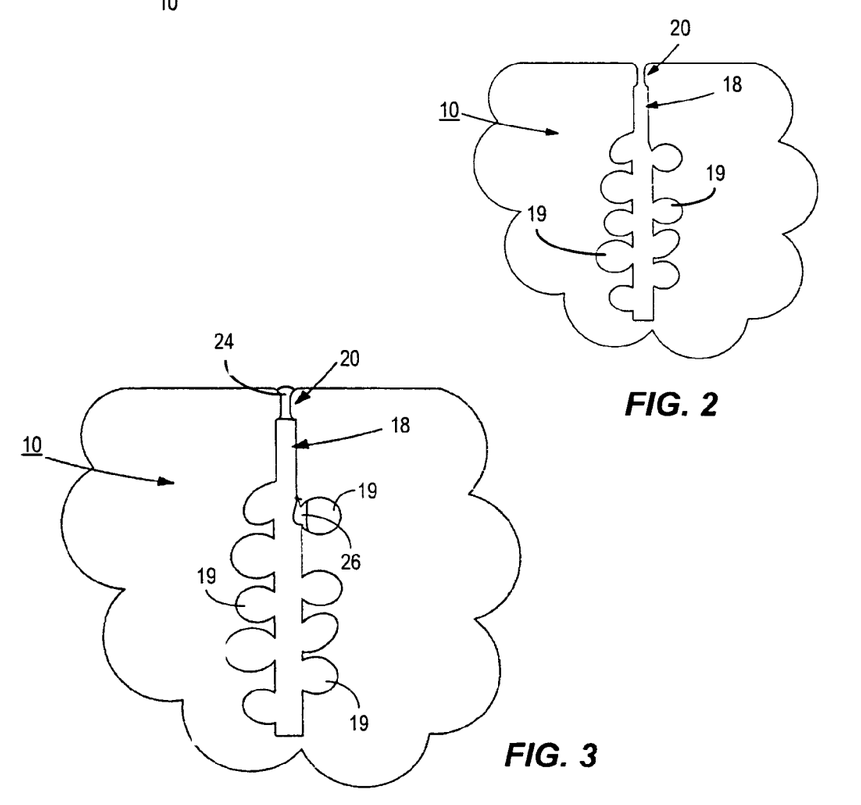
FIG. 2 is a cutaway view of an illustrative meibomian gland 20.
FIG. 3 is a cutaway view meibomian gland 20 illustrating several obstructed areas.

Obstruction composition will vary with the etiology which produced it. However, the obstruction will, in most cases observed to the present, be a combination of, dead cells, bacteria, desquamated cells, and desquamated cells aggregating in keratotic clusters, milky fluid, inspissated or creamy secretions, or any combination of the foregoing in solid, semi-solid and thickened forms. Referring to FIG. 3, a simplified view of exemplary obstructions to gland 10 are depicted. In this example, which is by no means necessarily representative of all meibomian gland obstructions, as explained above, a solid or semi-solid or thickened plug 24 is depicted which is fully occluding the orifice 20 of gland 10. Another obstruction 26 is shown at a junction from one of the acini with the central duct. As previously noted, this may be the site of a valve in the gland structure, but embodiments consistent with the present invention should not be limited by theories of the actual meibomian gland structure.

A number of treatment techniques have been proposed to restore these glands to normal functionality, but most doctors agree that heat is beneficial in treating MGD. Depending upon the nature of the obstruction, heat may be beneficial in actually melting or loosening the obstructing material or material binding solid particles to form the obstruction, permitting the gland to begin production and excretion of lipids and other fluids more freely. While the heat treatment methods described in the Background section hereof have been found to have many drawbacks, the heating techniques described in the above referenced copending applications have been found effective and beneficial. Generally speaking, these devices produce a regulated heating of the eyelid (as measured at the outer surface thereof) by direct contact with the eyelids to a therapeutic temperature of greater than 37 degrees Celsius, and more preferably between about 44 and 47 degrees Celsius with a target temperature of 45 degrees Celsius. However, other devices may be used which are placed proximate to the eyelids to provide heat to the meibomian glands.

The outside skin surface of the human eyelid has been observed to be approximately 1-2 degrees Celsius cooler than body temperature, with some variation. Increasing the temperature to at least 37 can begin to provide therapeutic effect for milder cases of MGD. One preferred range for treatment is 44 to 47 degrees Celsius, with a target of 45 degrees Celsius has been found effective and comfortable to the patient. In certain embodiments, the mechanical energy treating is carried out during or immediately after the end of the time period, and preferably with a heated instrument so as to maintain the more fluid state of the obstruction. Mechanical energy treatment can be carried out by any mechanism that induces mechanical pressures, including but not limited to vibratory, milking, mechanical pulsing pressure, squeezing and other actions to express fluids from the glands and/or dilate the duct or orifice of the meibomian gland. The mechanical energy can take any form that applies mechanical pressure on the meibomian glands to assist in pushing the blockage or obstruction out of the gland while the obstruction is softened by heat. Even higher temperatures (e.g., 50-55 degrees Celsius) can be used (or pulsed for short periods), especially if the eyelid has been anesthetized, in which case much hotter treatment for shorter time can be used without permanent injury to the patient. Generally, higher temperatures can be used for shorter periods of time. Moreover, the temperature and time used should be individualized based on the severity of the condition and the tolerance of the patient. It has been found that lighter skinned patients can generally tolerate less heat than darker skinned patients, and darker skinned patients tend to exhibit less inflammation as a result of exposure to the heat. Treatment times and/or temperature can be adjusted to account for these differences. Each of the above temperatures refers to the temperature as measured at the outer surface of the eyelid.

Also, in certain embodiments, the patient is more comfortable when the treatment begins at a lower temperature and the temperature is raised over time. Hence, the temperature should be regulated, where regulation should be interpreted to mean that the actual temperature applied at the outer surface of the eyelid is controlled or regulated in a manner that is repeatable. The temperature profile for heat application may be a constant temperature, or may have ramp-ups, ramp-downs, peaks, valleys, can be pulsed, or can be modulated with various characteristics, etc., but such profile should be regulated so as to be repeatable. It has also been found that modulating the temperature can result in a higher average temperature than a constant temperature, and may be useful in some applications.

This temperature can be maintained at a therapeutic temperature for a treatment period of approximately 10-60 minutes (or even beyond have been found safe and useful for some patients). Either during or after such treatment by controlled heat, mechanical expression of lipids and other fluids from the meibomian glands has been found to clear obstructions which have essentially melted or been placed in a suspension state (by virtue of melting materials binding solids together). The above applications disclose devices which generally apply a milking action to the eyelid to express the fluids or suspensions or to otherwise mechanically stimulate the movement of fluids from the glands—such fluid now including melted or suspended materials causing the obstructions or occlusions. In some instances, just gentle continuous force applied to the eyelid will assist in expression of the fluids and suspensions, while in others vibration can be used simultaneously or immediately after the heating. For purposes of this document, the term "melted" is to be interpreted to be inclusive of states in which solid particles remain suspended within a liquid fluid.

In certain embodiments, such devices that apply regulated heating of the eyelids are disclosed in U.S. patent application Ser. No. 11/434,054, filed May 15, 2006 and entitled Method and Apparatus for Treating Meibomian Gland Dysfunction to Korb, et al and U.S. patent application Ser. No. 11/434,033, filed May 15, 2006 entitled "Melting Meibomian Gland Obstructions", to Steve Grenon, et at, which are hereby incorporated by reference. In certain embodiments, that device utilizes a heater unit having a heating element that produces heat when an electrical signal is applied thereto. A temperature regulator applies the electrical signal to the heating element in order to achieve heating of the heating element to a specified temperature range. An eyelid interfacing mechanism couples the heater unit to the eyelid to achieve regulated heating of the eyelid within the specified temperature range.

Such a device provides regulated heating to a therapeutic temperature. Conventional hot compresses and the IR heating mechanisms described above background do not provide regulated controlled heating at a therapeutic temperature and are less effective than the regulated heat applied using the devices described in the above-referenced patent applications that are incorporated herein.

In another embodiment disclosed in this patent application, an apparatus that provides controlled heat to at least one of a patient's eyelids has a heater unit, and the heater unit having: a heating element having first and second surfaces that produces heat when an electrical signal is applied thereto; a thermal heat sink, coupled to the first surface of the heating element in order to transfer heat from the heating element to the eyelid; an insulator coupled to the second surface of the heating element in order to reduce heat loss from the second surface; and a back plate that couples to the insulator. A temperature regulator applies the electrical signal to the heating element in order to achieve heating of the heating elements to a specified temperature range. Goggles suitable for attaching to the patient's head and covering the eyelid of the patient with a lenspiece are provided with the lenspiece having a threaded aperture therein. A threaded shaft passes through the threaded lenspiece and coupled to the heater unit at the back plate so that the heater unit can be moved into contact with the eyelid by screwing the shaft into the aperture until contact with the eyelid is achieved.

Many variations in these embodiments are possible including, but not limited to, providing a sensor that senses temperature and provides temperature information to the temperature regulator. In certain embodiment the eyelid interfacing mechanism comprises goggles that are adjustably coupled to the heater unit in order to move the heater unit to achieve contact with the eyelid. The goggles may be adjustably coupled to the heater unit by a threaded connection so that a position of the heater unit can be adjusted by a threading action. In certain embodiments, the heater unit has a thermal heat sink, coupled to a surface of the heating element in order to transfer heat from the heating element to the eyelid. The thermal heat sink may be, for example, at least one of a thermally conductive rubber member, a thermally conductive silicon member, an encapsulated fluid containing member, and a solid conductive member. A thermally conductive gel, cream or liquid can be placed between the heat sink and the eyelid to enhance thermal conduction from the thermal heat sink to the eyelid.

In certain embodiments, the heater unit may have an insulator coupled to a surface of the heating element in order to reduce heat loss from the heating unit in a direction other than a direction toward the eyelid. The thermal insulator may be one of a non-thermally conductive foam element, a non-thermally conductive rubber element, and a non-thermally conductive solid element in certain embodiments. The temperature regulator may apply a pulse width modulated electrical signal to the heating element in order to regulate the heat produced thereby, and the pulse width modulated electrical signal may be produced under control of the control processor.

In certain embodiments, the temperature regulator may incorporate a switch that selectively applies the electrical signal to the heating element in order to regulate the heat produced thereby. The electrical signal may be at least one of a current and a voltage that is selectively applied to the heating element under control of a control processor. The heater unit may have a flexible portion that contacts the eyelid in order to conform to the eyelid or may have a rigid portion that contacts the eyelid, and wherein the rigid portion is shaped to conform to the shape of the eyelid, or a combination thereof.

The heater unit may have an adhesive for attaching the heater unit directly to the eyelid or may be attached to the eyelid by use of adhesive tape.

In certain embodiments, a user interface permits a user to establish at least one of a time and a temperature for the treatment. In certain embodiments, a vibration generator generates vibration of the eyelid to stimulate secretion from the meibomian glands, wherein the vibration generator may imparts mechanical energy to the eyelid having both an amplitude and frequency.

Other heating and/or pressure inducing devices are disclosed in the above-referenced patent applications which are incorporated herein by reference.

Hence, in view of the above, either immediately after treatment with heat, or during such heat treatment, -mechanical treatment using, for example, constant force, squeezing (e.g., by manual expression or otherwise), milking action or vibration can be applied to the eyelid to stimulate clearing of the fluids or suspensions from the meibomian glands. If mechanical treatment is carried out after heat treatment, it should be carried out immediately thereafter while the obstructive material of the meibomian gland is in a melted state.

Figure 4:
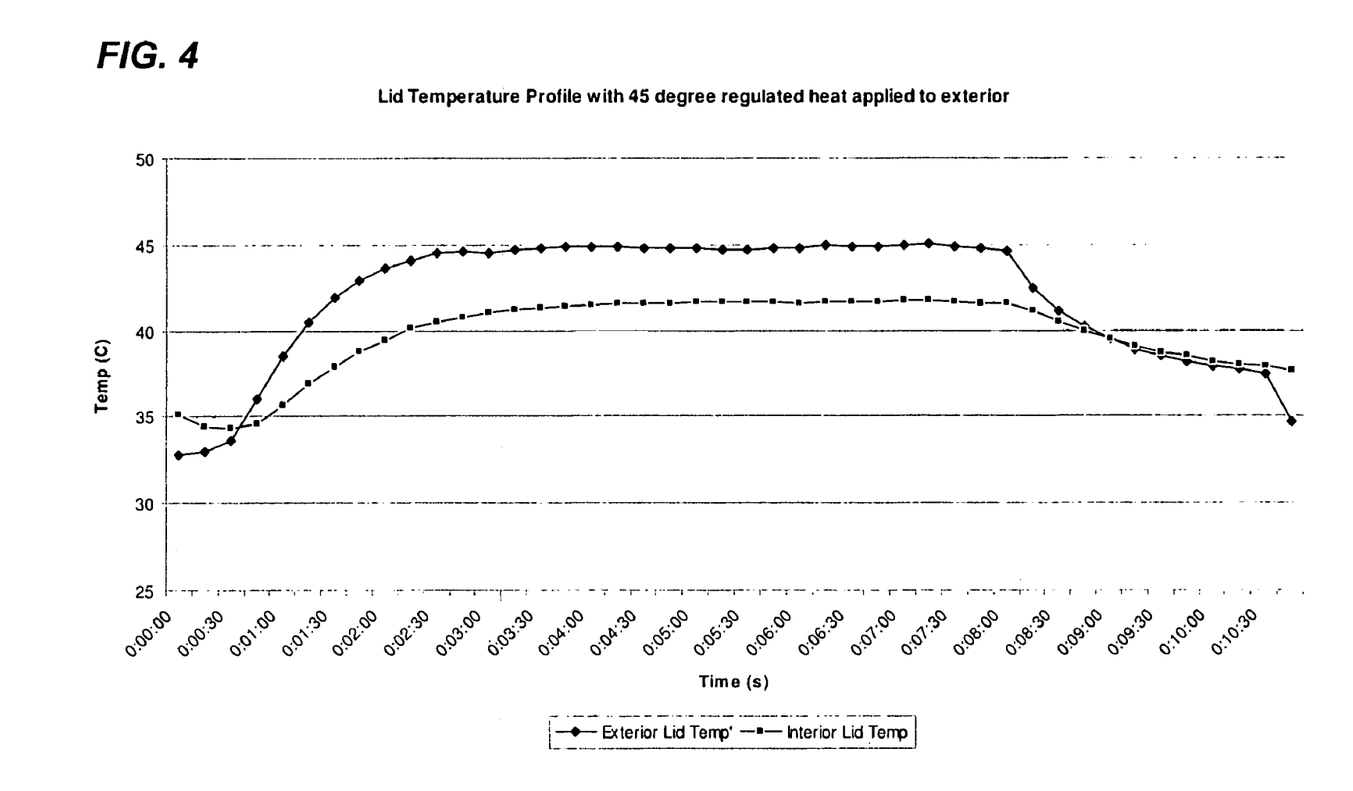
FIG. 4 is a graph of inner and outer surface temperatures of a patient's eyelid while the outer surface of the eyelid is heated to about 45 degrees C.

Referring now to FIG. 4, a graph depicts the inner surface of an eyelid and an outer surface of an eyelid when a source of constant heat at about 45 degrees C. was applied to an example subject patient. It should be noted that the circulatory system attempts to regulate the temperature of the eyelid, and blood flow increases with the application of heat. For this patient, it took approximately 4 minutes for the eyelid's outer surface to reach about 45 degrees Celsius, and the inner surface of the eyelid never reached this temperature—presumably because of the body's heat regulatory mechanisms. Hence, if a 45 degree constant heat source is used, it may take at least about 4 minutes to stabilize eyelid temperature and reach a therapeutic temperature.

It is also noted from this graph, that when the heat source is removed from the eyelid, the temperature drops very quickly to body temperature. In virtually all cases, this temperature will drop within 2-3 minutes, but more commonly, only about 30 seconds to 90 seconds are required for the patient's eyelid temperature to drop. In this example, the temperature dropped in temperature very quickly over the first thirty seconds after removal of the heat. During this short time period, some or all of the melted obstruction may re-solidify. Hence, if manual expression techniques are to be carried out subsequent to application of heat, the manual expression should follow immediately, or within about 90 seconds—with shorter intervals being preferred, e.g., within 30 seconds, or in any event, prior to reversal of the effects of the application of the regulated heat source such that at least a portion of the occlusion is removed. It will thus be clear from this graph that prior techniques of using warm compresses may be substantially less effective if manual expression does not follow within an extremely short period of time. Moreover, if the compresses cool below a therapeutic level prior to manual expression, they may provide minimal benefit to a patient suffering from substantial obstruction.

It has been discovered that the problem with most pharmacological treatment modalities for dry eye syndrome is that the pharmacological agent is unable to affect MGD when the disorder involves obstructions of the gland. That is, the currently known pharmaceutical treatments simply cannot unclog the meibomian glands to permit flow of lipids. While antibiotic treatment, steroid treatment, or other pharmacological treatments may be useful for other causes of dry eye, they have been found ineffective (or at most, to provide temporary symptomatic relief) when obstruction of the meibomian glands is involved. While many pharmacological agents may be useful in promoting lipid production and flow of the meibomian glands, such lipid production is not effective, and may be counterproductive if the secretion cannot get out of the gland. In fact, promoting lipid production may cause more meibomian difficulties and inflammation of the glands.

Other pharmacological agents may assist in promoting tear production or otherwise assisting in the lubricating function of the eye by promoting an improvement in the tear film. Used alone, such treatments may be ineffective or only partially effective, whereas, used after clearing of the meibomian glands may restore normal or near normal production of all components of the tear film. Hence, many pharmacological agents may be appropriate for further enhancement of the tear film and may be extremely beneficial once the meibomian glands are returned to more normal function.

Hence, once flow has been restored to the meibomian glands by heat and manual treatment (e.g., pressure during or after treatment, vibration, pulsation, manual expression, etc.), treatment with various pharmacological agents can be beneficial to maintaining the flow of lipids from the glands. Hence, with reference to FIG. 5, a treatment regimen is described starting at 100, after which a controlled heat such as produced by the various apparatus described in the above-referenced and incorporated by reference patent applications is applied to the eyelids at 104. The preferred heat is greater than 37 degrees Celsius, with a preferred range of heat between approximately 44-47 degrees Celsius, with a target of 45 degrees Celsius. However, greater temperatures Celsius for shorter periods of time will provide therapeutic benefit, with the possible side effect of minor skin burns that do not cause lasting damage. Below this temperature range, treatment tends to be less effective or ineffective. Temperatures above this range can cause substantial patient discomfort, injury to the eyelids and possibly the eye. At higher temperatures within the range, the patient may find the heat to be somewhat uncomfortable, but the treatment time can be reduced and the discomfort can be moderated with anesthetic. Lower temperatures in the range are effective but generally take a longer heating period.

Figure 5:
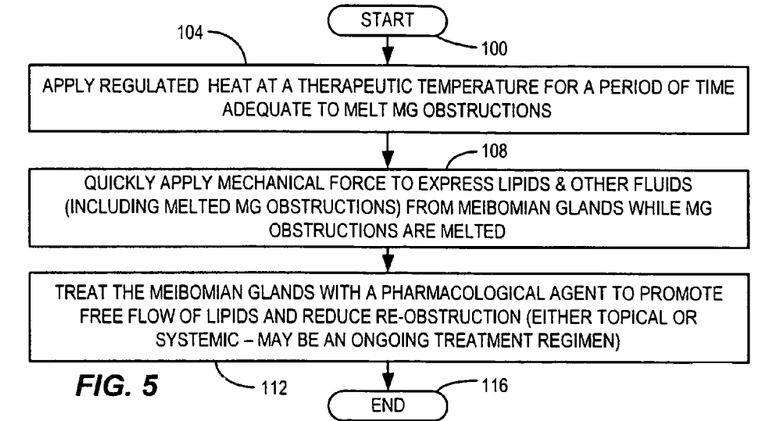
FIG. 5 is a flow chart depicting a treatment process consistent with certain embodiments of the present invention.

As a rule of thumb starting point, fifteen minutes at a relatively constant 45 degrees generally works well for many patients with mild to moderate MGD without undue patient discomfort. Time ranges from about 10-60 minutes or even beyond may be used depending upon the severity of the MGD condition, the temperature, anesthetic used and patient tolerance. In experiments, times beyond one hour were used without apparent adverse effects.

Once the heat treatment is completed (and/or during the heat treatment), mechanical force can be applied at 108 in any of the above mechanical modalities discussed to express the fluids or suspensions from the meibomian glands while the obstructions are in the melted state. When expression of the glands is used, it is preferable that any instrument used in the expression process be heated so as to simultaneously apply or assist in maintaining heat to the glands at the time of expression.

While manual expression of the gland can be painful and is invasive with inconsistent results when used alone due to variations in manual control and/or manipulation, and while this method of treating MGD can also be quite uncomfortable to the patient because it requires the physician to squeeze the glands, this technique may prove useful as a step in the process used selectively in difficult cases. There are about 45-50 glands between the upper and lower lid, therefore, it is very time consuming to squeeze each gland and therefore inefficient for the physician and uncomfortable for the patient to endure. However as noted, it may be beneficial in combination with automated expression devices to assist in further clearing severely obstructed glands to enhance the normal flow of lipids flowing through the orifices and out of the glands to the tear film. After heat treatment, the expression of secretions from an obstructed gland is generally dramatically more effective with less patient discomfort and better results, than if used alone. As noted previously, when expression of the glands is used, it is preferable that any instrument used in the expression process be heated so as to simultaneously apply heat or assist in maintaining heat to the glands at the time of expression.

Once the occlusions and other foreign substances have been cleared from the meibomian glands at 104 and 108 and lipid flow is restored, the meibomian glands can be treated with any of a variety of pharmacological agents, either topical or systemic) in order to minimize inflammation of the glands, clear infections, prevent further blockages, thin the lipids, promote production of tears, enhance the composition of the tear film, or any other pharmacological modality that promotes the free flow of the lipids or enhanced lubrication of the eye at 112. Pharmacological treatment may be carried out either for a short duration (e.g., to clear an infection or inflammatory condition), or for ongoing therapy (e.g., as in pharmacological agents that thin the lipids, reduce inflammation or treat other modalities of dry eye syndrome). This process ends at 116.

Many pharmacological agents have been proposed for treatment of dry eye syndrome, any of which may be effective or more effective upon clearing of obstructions within the meibomian glands. Some of the pharmacological agents that may be utilized include, but are not limited to: antibiotics such as topical or oral tetracycline and chemically modified tetracycline, testosterone, topical or oral corticosteroids; topical androgens or androgen analogues, omega 3 fatty acid compounds such as fish oils, laennec, enzymes that promote lipid production, agents that stimulate production of enzymes that promote lipid production, and any agent which acts as a secretagogue to enhance meibomian gland secretion or secretion of other tear components. Androgen and androgen analogues and TGF-β have been reported to act as a secretagogue to enhance meibomian gland secretion, agents that replace or promote production of any tear component, and there are likely many others. These compounds are illustrative examples of appropriate pharmacological agents, but those skilled in the art will appreciate that other pharmacological compounds may be utilized upon consideration of the present teachings. It is further noted that multiple modalities may be involved in causing dry eye syndrome, but treatment of only one modality may not result in full resolution. Hence, the restoration of normal or near normal lipid flow from the meibomian glands may be only a part of the solution—with pharmacological treatment of the other modality or modalities of the disease restoring a normal tear film. However, when significant MG dysfunction is involved, treatment of the other modalities alone is likely to be less than satisfactory.

A variation of the above treatment is described in connection with FIG. 6 starting at 130, after which a controlled heat such as produced by the various apparatus described in the above-referenced and incorporated by reference patent applications is applied to the eyelids at 104 as in the prior treatment method. The preferred range of such heat is again between approximately 44-47 degrees Celsius, with a target of 45 degrees Celsius. Again, time ranges from about 10 to 60 minutes and beyond may be used, depending upon severity of the condition, the treatment temperature and patient tolerance.

In this embodiment, during the heat treatment, mechanical force can be applied at 138 in any of the above mechanical modalities discussed, including those referenced and incorporated by reference, to express the fluids or suspensions from the meibomian glands while the obstructions are in a liquid or suspension state during application of the heat.

Depending upon the patient response to heat in combination with simultaneous mechanical force at 138, additional force can be applied immediately subsequent to removal of the heat at 142. In this case, it is also preferred that heat be maintained during the time of expression or force being applied as described. That is, it is preferred that any probe or other instrument used during the expression be heated to help maintain the obstruction in a liquid or suspension state. Such force can be manually applied by squeezing the eyelids at appropriate locations where obstructions appear to remain, or automated mechanical means may be employed if available.

Once the occlusions and foreign substances have been cleared from some or all of the meibomian glands at 104, 138 and 142, the meibomian glands can be treated with any of a variety of pharmacological agents, either topical or systemic) in order to minimize inflammation of the glands, clear infections, prevent further blockages, thin the lipids or any other pharmacological modality that promotes the free flow of the lipids or otherwise promote an improved tear film at 112 as before. As noted, pharmacological treatment may be carried out either for a short duration (e.g., to clear an infection or inflammatory condition), or for ongoing therapy (e.g., as in pharmacological agents that thin the lipids, improve the tear composition, or reduce inflammation). This process ends at 150.

Figure 6:
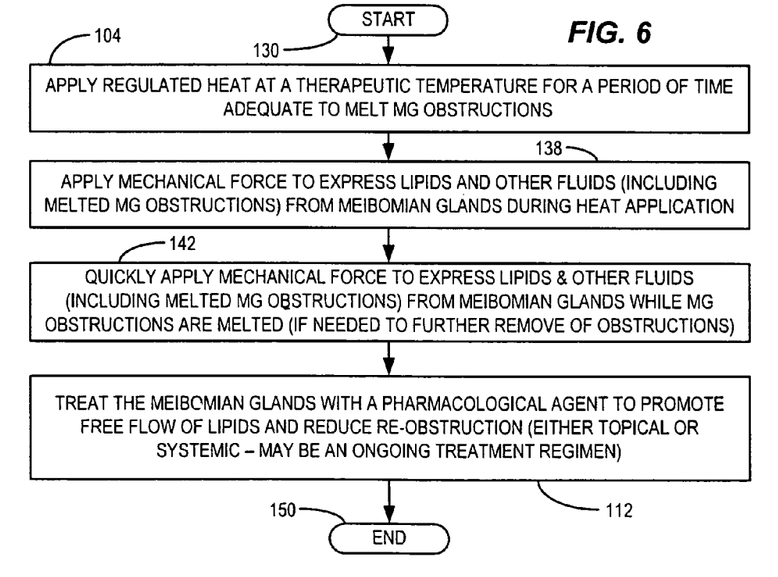
FIG. 6 is a flow chart depicting another treatment process consistent with certain embodiments of the present invention.

The above processes, whether involving the process of FIG. 5 or FIG. 6, may be repeated or interchanged at time intervals as needed to create or maintain proper flow from the meibomian glands. Such treatments, or portions thereof, may need to be periodically repeated for some patients in order to keep the lipids flowing from the meibomian glands.

Thus, in accordance with certain embodiments consistent with the present invention, a method of treating mammalian meibomian glands involves clearing the glands by applying a regulated heat to an eyelid containing the meibomian glands to reach a temperature adequate to melt obstructions in the meibomian glands and maintaining the heat for a time period adequate to melt the obstructions and place the obstructions in a fluid or suspension (melted) state. The glands can then be mechanically treated to express fluid or suspension from the glands, wherein the mechanical treatment is carried out either during the time period or after the time period but while the obstruction remains in the melted state. The process may be enhanced by a heated treatment device for applying the force to maintain the temperature and the melted state of the obstructive material. Subsequent pharmacological treatment of the glands by use a pharmacological agent (topical or systemic) can then be used to assist in maintaining proper flow of lipids from the glands.

In accordance with certain embodiments, the time period can be approximately 10 to 60 minutes, and approximately 15 minutes is generally suitable for mild to moderate cases. The temperature should be greater than 37 degrees Celsius and the preferred range is approximately 44 to 47 degrees Celsius with a target of 45 degrees Celsius at the eyelid's outer surface has been found effective and comfortable to the patient. In certain embodiments, the mechanical treating is carried out as soon as possible after the heating, and preferably within about 30-90 seconds, so that the obstruction will remain in a melted state during the expression process. In other embodiments, the mechanical treatment is carried out by at least one of application of constant pressure, squeezing, milkingly expressing the fluid or suspension from one or more of the glands while simultaneously applying heat, or applying vibratory stimulation to the eyelid while simultaneously applying heat. Many variations and alternative embodiments will occur to those skilled in the art upon consideration of the present teaching.

While certain illustrative embodiments have been described, it is evident that many alternatives, modifications, permutations and variations will become apparent to those skilled in the art in light of the foregoing description.

What is claimed is:

1. A method of treating mammalian meibomian glands having a meibomian gland channel and a meibomian gland orifice at a top of the meibomian gland channel, comprising:
applying regulated heat to an eyelid containing the meibomian glands that reaches a temperature adequate to melt obstructions within the meibomian gland channel of the meibomian glands and place the obstructions in a melted state;
maintaining the heat for a time period adequate to melt the obstructions and place the obstructions in the melted state;
mechanically treating one or more of the meibomian glands by expressing the melted obstructions located within the meibomian gland channel from within the meibomian gland channel through the meibomian gland orifice using a compressive force, wherein the mechanical treating is carried out either during the time period or after the time period but while the obstruction remains in the melted state; and
subsequently treating the meibomian glands by use of a pharmacological agent.

2. The method according to claim 1, wherein the time period comprises approximately 10 to 60 minutes.

3. The method according to claim 1, wherein the mechanical treatment is carried out using a heated instrument.

4. The method according to claim 1, wherein the temperature reaches approximately 45 degrees Celsius.

5. The method according to claim 1, wherein the temperature reaches between approximately 44 and 47 degrees Celsius.

6. The method according to claim 1, wherein the temperature is at least 37 degrees Celsius.

7. The method according to claim 1, wherein the mechanical treating is carried out within 3 minutes after the end of the time period.

8. The method according to claim 1, wherein the mechanical treatment is carried out by milkingly expressing the melted obstructions located within the meibomian gland channel from within the meibomian gland channel through the meibomian gland orifice of one or more of the meibomian glands.

9. The method according to claim 1, wherein the pharmacological agent comprises a topical pharmacological agent.

10. The method according to claim 1, wherein the pharmacological agent comprises a systemic pharmacological agent.

11. The method according to claim 1, wherein the pharmacological agent is selected from the group consisting of antibiotics, topical tetracycline, oral tetracycline, topical corticosteroids, oral corticosteroids, topical androgens, topical androgen analogues, TGF-.beta., omega 3 compounds, enzymes that promote lipid production, agents that stimulate production of enzymes that promote lipid production, agents that act as a secretagogue to enhance Meibomian gland secretion, and agents that replace or promote production of any tear component.

12. The method according to claim 11, wherein a plurality of said pharmacological agents are selected.

13. The method according to claim 1, further comprising repeating the applying and maintaining of regulated heat after a time interval to maintain flow of fluids from the meibomian glands.

14. The method according to claim 13, further comprising repeating the mechanical treating at the time interval to maintain flow of fluids from the meibomian glands.

15. The method according to claim 1, wherein the mechanical treatment is carried out by applying mechanical energy stimulation to the eyelid.

16. The method according to claim 1, wherein the mechanical treatment is carried out by squeezing the eyelid and applying constant compressive force to the eyelid.

17. A method of treating mammalian meibomian glands having a meibomian gland channel and a meibomian gland orifice at a top of the meibomian gland channel, comprising:
applying a regulated heat of at least approximately 37 degrees Celsius to an eyelid containing the meibomian glands to melt obstructions within the meibomian gland channel of the meibomian glands and place such obstructions in a melted state;
maintaining the heat for a time period adequate to melt the obstructions and place the obstructions in the melted state, and wherein the time period is between approximately 10 and 60 minutes;
mechanically treating one or more of the meibomian glands by expressing the melted obstructions located within the meibomian gland channel from within the meibomian gland channel through the meibomian gland orifice using a compressive force, wherein the mechanical treating is carried out prior to 90 seconds after expiration of the time period and while the obstruction remains in the melted state; and
subsequently pharmacologically treating the meibomian glands by use a pharmacological agent.

18. The method according to claim 17, wherein the temperature reaches approximately 44 to 47 degrees Celsius.

19. The method according to claim 17, wherein the temperature reaches approximately 45 degrees Celsius.

20. The method according to claim 17, wherein the mechanical treatment is carried out by milkingly expressing the melted obstructions located within and from within the meibomian gland channel through the meibomian gland orifice of one or more of the meibomian glands.

21. The method according to claim 17, wherein the pharmacological agent comprises a topical pharmacological agent.

22. The method according to claim 17, wherein the pharmacological agent comprises a systemic pharmacological agent.

23. The method according to claim 17, wherein the mechanical treatment is carried out using a heated instrument.

24. The method according to claim 17, wherein the pharmacological agent is selected from the group consisting of antibiotics, topical tetracycline, oral tetracycline, topical corticosteroids, oral corticosteroids, topical androgens, topical androgen analogues, TGF-.beta., omega 3 compounds, enzymes that promote lipid production, agents that stimulate production of enzymes that promote lipid production, agents that act as a secretagogue to enhance Meibomian gland secretion, and agents that replace or promote production of any tear component.

25. The method according to claim 24, wherein a plurality of said pharmacological agents are selected.

26. The method according to claim 17, wherein the mechanical treatment is carried out by applying vibratory stimulation to the eyelid.

27. The method according to claim 17, wherein the mechanical treatment is carried out by squeezing the eyelid and applying constant compressive force to the eyelid.

28. The method according to claim 17, wherein the mechanical treatment is carried out by pulsating compressive force to the eyelid.

29. A method of treating mammalian meibomian glands having a meibomian gland channel and a meibomian gland orifice at a top of the meibomian gland channel, comprising:
applying a regulated heat in the range of approximately 44 to 47 degrees Celsius to an eyelid containing the meibomian glands to melt obstructions within the meibomian gland channel of the meibomian glands and place the obstructions in a melted state;
maintaining the heat for a time period adequate to melt the obstructions and place the obstructions in the melted state, wherein the time period is between approximately 10 and 60 minutes;
mechanically treating one or more of the meibomian glands by expressing fluid or suspension of the obstructions located within the meibomian gland channel from within the meibomian gland channel through the meibomian gland orifice using a compressive force, wherein the mechanical treating is carried out either during the time period or within 90 seconds following the end of the time period while the obstruction remains in the melted state, wherein the mechanical treating is carried out using a heated instrument; and
subsequently, pharmacologically treating the meibomian glands by use a pharmacological agent.

30. The method according to claim 29, wherein the mechanical treatment is carried out by milkingly expressing the fluid or suspension located within the meibomian gland channel from the meibomian gland channel through the meibomian gland orifice of one or more of the meibomian glands.

31. The method according to claim 29, wherein the pharmacological agent comprises a topical pharmacological agent.

32. The method according to claim 29, wherein the pharmacological agent comprises a systemic pharmacological agent.

33. The method according to claim 32, wherein a plurality of said pharmacological agents are selected.

34. The method according to claim 29, wherein the pharmacological agent is selected from the group consisting of antibiotics, topical tetracycline, oral tetracycline, topical corticosteroids, oral corticosteroids, topical androgens, topical androgen analogues, TGF-.beta., omega 3 compounds, enzymes that promote lipid production, agents that stimulate production of enzymes that promote lipid production, agents that act as a secretagogue to enhance Meibomian gland secretion, and agents that replace or promote production of any tear component.

35. The method according to claim 29, further comprising repeating the applying and maintaining regulated heat after a time interval.

36. The method according to claim 35, further comprising repeating the mechanically treating at the time interval to maintain flow of fluids from the meibomian glands.

37. The method according to claim 29, wherein the mechanical treatment is carried out by applying mechanical energy stimulation to the eyelid.

38. The method according to claim 29, wherein the mechanical treatment is carried out by applying vibratory energy to the eyelid.

39. The method according to claim 29, wherein the mechanical treatment is carried out by applying constant compressive force or pulsating compressive force to the eyelid.

40. A method of treating meibomian gland dysfunction in a mammal wherein an occlusion blocks at least a portion of the flow of naturally occurring secretions out of a meibomian gland channel having a meibomian gland orifice comprising:
a) applying a regulated heat source proximate to the meibomian gland orifice for a selected time and at a selected temperature adequate to soften or liquefy at least a portion of the occlusion;
b) mechanically treating the meibomian gland channel while the at least a portion of the occlusion remains softened or liquefied such that at least a portion of the occlusion located within the meibomian gland channel is removed from within the meibomian gland channel through the meibomian gland orifice using a compressive force; and
c) subsequently treating the mammal with a pharmacological agent which promotes the free flow of lipids from the meibomian gland.

41. The method according to claim 40, wherein the selected time comprises approximately 10 to 60 minutes.

42. The method according to claim 40, wherein the selected temperature reaches between approximately 44 and 47 degrees Celsius.

43. The method according to claim 40, wherein the selected temperature is at least 37 degrees Celsius.

44. The method according to claim 40, wherein the pharmacological agent comprises a topical pharmacological agent.

45. The method according to claim 40, wherein the pharmacological agent comprises a systemic pharmacological agent.

46. A method of treating meibomian gland dysfunction in a mammal wherein an occlusion blocks at least a portion of the flow of naturally occurring secretions out of a meibomian gland channel having a meibomian gland orifice comprising:
a) applying a regulated heat source proximate to the meibomian gland orifice for a selected time and at a selected temperature adequate to loosen, breakup, fracture, soften or liquefy at least a portion of the occlusion;
b) mechanically treating the meibomian gland channel prior to reversal of the effects of the application of the regulated heat source such that at least a portion of the occlusion located within the meibomian gland channel is removed from within the meibomian gland channel through the meibomian gland orifice using a compressive force; and
c) subsequently treating the mammal with a pharmacological agent which promotes the free flow of lipids from the meibomian gland.

47. The method according to claim 46, wherein the time period comprises approximately 10 to 60 minutes.

48. The method according to claim 46, wherein the temperature reaches between approximately 44 and 47 degrees Celsius.

49. The method according to claim 46, wherein the pharmacological agent comprises a topical pharmacological agent.

50. The method according to claim 46, wherein the pharmacological agent comprises a systemic pharmacological agent.

* * * * *